United States Patent
Ma (10) Patent No.: US 8,449,507 B2
(45) Date of Patent: May 28, 2013

(54) DISPOSABLE ANALGESIC AND LOCAL ANESTHETIC UNDERGARMENT

(75) Inventor: Edna Ma, Los Angeles, CA (US)

(73) Assignee: Miss Smarty Pants Enterprises, Inc., Los Angeles, CA (US)

(*) Notice: Subject to any disclaimer, the term of this patent is extended or adjusted under 35 U.S.C. 154(b) by 290 days.

(21) Appl. No.: 12/022,787

(22) Filed: Jan. 30, 2008

(65) Prior Publication Data

US 2009/0062753 A1   Mar. 5, 2009

Related U.S. Application Data

(60) Provisional application No. 60/968,442, filed on Aug. 28, 2007.

(51) Int. Cl.
| A61M 35/00 | (2006.01) |
| A61F 13/15 | (2006.01) |
| A61F 13/00 | (2006.01) |
| A61L 15/44 | (2006.01) |

(52) U.S. Cl.
CPC .......... *A61M 35/00* (2013.01); *A61F 13/00004* (2013.01); *A61F 13/00* (2013.01); *A61L 15/44* (2013.01)
USPC .......................................... 604/290; 604/396

(58) Field of Classification Search
USPC ........................... 604/289–290, 359–360, 364
See application file for complete search history.

(56) References Cited

U.S. PATENT DOCUMENTS

| 4,014,338 | A | | 3/1977 | Schaar |
| 4,341,208 | A | | 7/1982 | Gordon |
| 4,623,339 | A | * | 11/1986 | Ciraldo et al. ................ 604/359 |
| 4,699,146 | A | * | 10/1987 | Sieverding .................... 600/391 |
| 5,073,365 | A | * | 12/1991 | Katz et al. .................... 427/2.24 |
| 5,538,783 | A | * | 7/1996 | Hansen et al. ................ 442/417 |
| 6,068,607 | A | | 5/2000 | Palmer et al. |
| 6,120,488 | A | * | 9/2000 | VanRijswijck et al. .. 604/385.28 |
| 6,120,783 | A | * | 9/2000 | Roe et al. ...................... 424/402 |
| 6,149,934 | A | * | 11/2000 | Krzysik et al. ................ 424/443 |
| 6,166,285 | A | * | 12/2000 | Schulte et al. ................ 604/364 |
| 6,369,291 | B1 | | 4/2002 | Uchimoto et al. |
| 6,409,713 | B1 | | 6/2002 | Osborne, III et al. |
| 6,475,201 | B2 | | 11/2002 | Saito et al. |
| 6,514,233 | B1 | | 2/2003 | Glaug |
| 6,592,879 | B2 | * | 7/2003 | Moehring ..................... 424/400 |
| 6,811,549 | B2 | | 11/2004 | Fleming |

(Continued)

FOREIGN PATENT DOCUMENTS

| GB | 1471987 | | 4/1977 |
| WO | WO 0145613 A1 | * | 6/2001 |
| WO | 0222104 A2 | | 3/2002 |
| WO | 02/063984 A3 | | 1/2003 |

OTHER PUBLICATIONS

Derwent abstract, CA200998450, Jan. 2, 2008.*

*Primary Examiner* — Susan Su
(74) *Attorney, Agent, or Firm* — Fox Rothschild LLP (57) ABSTRACT

A method for delivering a local anesthetic to a body part includes applying the local anesthetic to an inner portion of a disposable undergarment having a corrugated region in front of the disposable undergarment, wherein the local anesthetic fills at least one pocket of the corrugated region. The method includes covering the body part with the disposable undergarment such that the local anesthetic is subsequently released from the corrugated region and is absorbed percutaneously into the body part to allow numbing of the body part.

5 Claims, 5 Drawing Sheets

U.S. PATENT DOCUMENTS

| | | | |
|---|---|---|---|
| 6,939,553 B2 * | 9/2005 | Yahiaoui et al. | 424/402 |
| 6,992,233 B2 | 1/2006 | Drake et al. | |
| 7,033,645 B2 | 4/2006 | Gatto et al. | |
| 7,060,867 B2 * | 6/2006 | Jameson | 604/364 |
| 7,250,549 B2 | 7/2007 | Richlen et al. | |
| 2002/0087129 A1 * | 7/2002 | Di Luccio et al. | 604/304 |
| 2002/0120242 A1 | 8/2002 | Tyrrell et al. | |
| 2003/0120225 A1 * | 6/2003 | Everhart et al. | 604/285 |
| 2004/0122401 A1 | 6/2004 | Van Gompel et al. | |
| 2004/0208984 A1 | 10/2004 | Gatto et al. | |
| 2005/0137563 A1 | 6/2005 | Van Gompel et al. | |
| 2006/0100593 A1 | 5/2006 | Bridges | |
| 2008/0147027 A1 * | 6/2008 | Sanabria et al. | 604/358 |

* cited by examiner

DISPOSABLE ANALGESIC AND LOCAL ANESTHETIC UNDERGARMENT

CROSS-REFERENCE TO RELATED APPLICATIONS

This application claims the benefit of Provisional Patent Application Ser. No. 60/968,442, entitled "Disposable Analgesic, Local Anesthetic Undergarments," to inventor Edna Ma, filed Aug. 28, 2007, all the contents of which are incorporated herein by this reference.

FIELD OF INVENTION

This invention relates, generally, to disposable undergarments. Moreover, it pertains specifically to a disposable undergarment, such as women's panties or men's briefs, which are lined with local anesthetics that create an area or areas of numbness on the body.

BACKGROUND

For centuries people have used undergarments to protect sensitive skin, absorb incontinent discharges, and provide for the modesty of the wearer. One challenge faced by designers of lower body undergarments is how to provide comfort and protection to people who are about to undergo or who have recently undergone surgery or some other painful procedure, such as hair removal waxing, in the groin region. Another challenge is how to easily, safely, accurately, and comfortably deliver pain relief to people who are about to undergo or who have recently undergone surgery or some other painful procedure, such as hair removal waxing, in the groin region. Two common types of protective undergarments are cups, or other undergarments with plastic inserts, and diapers. Although cups and diapers may provide some groin protection, they are bulky, uncomfortable, and frequently noticeable. Another problem with cups and diapers is that they are not conducive to the delivery of a local anesthetic or analgesic to pained areas of the groin. Further, if a local anesthetic is applied directly to the undergarment or skin of pained areas of the groin, it is likely that the anesthetic will stain both the undergarment and the outer clothing. Local anesthetics are most effective when they are held in contact with the user's skin for an extended duration. Percutaneous absorption of local anesthetics is also enhanced by an occlusive dressing. This improves the effectiveness of the local anesthetic and requires the use of less local anesthetic to accomplish the numbing task. It is both safer and less expensive to use less local anesthetic. Currently available undergarments do not function as an occlusive dressing. In fact, it is likely that the anesthetic's effectiveness will be minimized because the undergarment or outer clothing will absorb the anesthetic rather than releasing it to the pained areas of the groin. Absorption of the local anesthetic by the clothing or undergarment will impair the effectiveness of the local anesthetic, not allow for appropriate numbing of the user, and increase expense cause by repeated applications. Finally, application directly to the groin is messy and may require the user to wear gloves to protect his or her fingers from the numbing effects of the anesthetic. Thus, it is clear that there is a need in the art for a disposable undergarment that can easily, safely, accurately, and comfortably administer a local anesthetic to pained regions of the groin or a region of the groin about to undergo a painful procedure.

In the area of applying a local anesthetic to a body part that is about to undergo a painful procedure, such as waxing or piercing, many people use plastic or SARAN wrap to hold the numbing agent fast to the body. However, using plastic or SARAN wrap to hold a numbing agent or anesthetic fast to the body is clumsy, messy, and bulky. If this method is used in the groin area, the simple task of urination becomes an extended chore where the plastic wrap has to be completed removed. Often the user of this method has to redo completely the application of the anesthetic and plastic wrapping. Thus, it is clear that the method of using plastic or SARAN wrap to hold a numbing agent fast to the body is not an easy, safe, efficient, or comfortable way to administer a local anesthetic to pained regions of the groin or a region of the groin about to undergo a painful procedure.

In the area of percutaneous delivery systems, numerous bandages have been developed that allow an injured person to apply a bandage that is pre-treated with a therapeutic. One such bandage system is disclosed by U.S. Pat. No. 6,992,233 to Drake et al., which discloses system for delivering a therapeutic or medicine to the surface of the skin. Drake's bandage adhesively attaches to the user and only applies the therapeutic or medicine to a limited area. Although Drake discloses a percutaneous delivery system, Drake fails to disclose this system wherein the therapeutic or medicine is an anesthetic, or wherein the bandage is a disposable undergarment.

Another percutaneous delivery system is disclosed by U.S. Pat. No. 4,341,208 to Gordon, which discloses a liquid impermeable bandage for delivering an ointment to the surface of the skin. Although Gordon's bandage is liquid impermeable, and thus protects the user's clothing from the ointment, Gordon fails to disclose this system wherein the ointment is an anesthetic, or wherein the bandage is a disposable undergarment.

Another delivery system is disclosed by U.S. Pat. No. 6,811,549 to Fleming, and U.S. Pat. No. 6,409,713 to Osborne III et al., which recite the application or administration of therapeutic agents using an interlabial pad. Although this type of delivery system is specific to the groin, it fails to reference the use of disposable undergarments.

In the area of disposable undergarments, several types have been developed that allow the user to discard the undergarment when the user is finished wearing it. One such disposable undergarment is U.S. Pat. No. 6,475,201 to Saito et al., which discloses a disposable underwear article that is worn and then discarded by the wearer. However, Saito fails to disclose a disposable undergarment lined with an anesthetic.

Another type of disposable undergarment is the diaper. U.S. Pat. No. 6,369,291 to Uchimoto et al., U.S. Pat. No. 6,514,233 to Glaug, and U.S. Pat. No. 7,250,549 to Richlen, are three examples of disposable diaper type undergarments. Although these diapers are disposable and provide the user some groin protection, Uchimoto, Glaug, and Richlen fail to teach an undergarment that is lined with an anesthetic.

Another type of diaper is disclosed by U.S. Pat. No. 7,033,645 to Gatto et al., which discloses a disposable diaper with a skin care agent. The skin care agent is transferred to the user of the diaper and this helps prevent diaper rash. However, the Gatto diaper fails to teach an undergarment that is lined with an anesthetic. In fact, Gatto specifically requires the diaper to be lined with a skin enhancing emulsion.

A final type of undergarment is disclosed by U.S. Pat. No. 6,068,607 to Palmer et al., which discloses an undergarment that has a removable cold compress to cool the genitalia of the user. The Palmer cooling undergarment system allows the user to remove the cold compress so that it can be re-cooled and re-used numerous times. Although Palmer discloses an undergarment with therapeutic properties, it fails to disclose a disposable undergarment that is lined with an anesthetic that is absorbed into the skin.

Thus, there remains a long-felt need in the art for a disposable undergarment that can easily, safely, accurately, and comfortably administer a local anesthetic to pained regions of the groin or a region of the groin about to undergo a painful procedure.

SUMMARY OF THE INVENTION

To minimize the limitations in the prior art, and to minimize other limitations that will become apparent upon reading and understanding the present specification, the present invention discloses disposable undergarments, such as women's panties or men's briefs, which are lined with local anesthetics that create an area or areas of numbness on the body.

In one embodiment, the invention is a disposable undergarment, comprising an inner portion and an outer portion, wherein the inner portion is lined with a local anesthetic. Such a disposable undergarment wherein the inner portion is divided into a plurality of regions. Such a disposable undergarment wherein the plurality of regions are separately covered with removable covers. Such a disposable undergarment wherein the plurality of regions are lined with differing concentrations of the local anesthetic. Such a disposable undergarment wherein there is a plurality of local anesthetics, and wherein the plurality of regions are lined with different types of the plurality of local anesthetics. Such a disposable undergarment wherein the outer portion is impermeable to the local anesthetic to protect clothing worn over the disposable undergarment.

In one embodiment, the invention is a disposable undergarment comprising an inner portion and an outer portion, wherein the inner portion is corrugated and lined with a local anesthetic. Such a disposable undergarment wherein the corrugated inner portion is divided into a plurality of regions. Such a disposable undergarment wherein the plurality of regions are separately covered with removable covers. Such a disposable undergarment wherein the plurality of regions are lined with differing concentrations of the local anesthetic. Such a disposable undergarment wherein there is a plurality of local anesthetics, and wherein the plurality of regions are lined with different types of the plurality of local anesthetics. Such a disposable undergarment wherein the outer portion is impermeable to the local anesthetic to protect clothing worn over the disposable undergarment.

In one embodiment, the invention is a method for delivering a local anesthetic to a body part comprising applying the local anesthetic to an inner portion of a disposable undergarment, donning the disposable undergarment, and allowing the local anesthetic to numb the body part. In another embodiment, the method for delivering the local anesthetic to the body part further comprises applying the local anesthetic to the inner portion in differing concentrations to a plurality of regions of the inner portion.

A principal object of the present invention is to provide disposable local anesthetic undergarments that will overcome the deficiencies of the prior art.

Another object of the present invention is to provide disposable local anesthetic undergarments, which can be worn by a user and will thereby act to reduce pain associated with waxing, laser hair removal, tattoos, piercings, post groin operations, post circumcision operations, and post vaginal or labial rejuvenations.

Another object of the present invention is to provide disposable local anesthetic undergarments, which holds a local anesthetic in direct contact with the skin for a sufficient duration to make the skin numb. The disposable local anesthetic undergarments will function in the same manner as an occlusive dressing.

Another object of the present invention is to provide disposable local anesthetic undergarments that can be used by both men and women to manage or minimize pain associated with various medical or personal procedures, such as hair removal waxing.

Another object of the present invention is to provide disposable local anesthetic undergarments, which can be worn by a user and will thereby act to help patients who suffer from pre-mature ejaculation or who wish to delay ejaculation during coitus.

Another object of the present invention is to provide disposable local anesthetic undergarments that can be worn discretely under normal clothing.

Another object of the present invention is to provide disposable local anesthetic undergarments that will allow a user to numb certain areas of their body in a clean, discrete, private, and mess free manner.

Another object of the present invention is to provide disposable local anesthetic undergarments that are less messy and cumbersome than existing products and keeps regular garments clean.

Another object of the present invention is to provide disposable local anesthetic undergarments where the anesthetic works more quickly than prior art devices.

Another object of the present invention is to provide disposable local anesthetic undergarments that allow for the administration of an anesthetic to a user's body in a hands free manner.

Another object of the present invention is to provide disposable undergarments that are receptive to local anesthetics, but which are provided without local anesthetics. This allows user's to choose which specific local anesthetic to apply.

Another object of the present invention is to provide corrugated disposable undergarments that are receptive to local anesthetics, but which are provided without local anesthetics. This allows user's to choose which specific local anesthetic to apply into the corrugations.

Another object of the present invention is to provide disposable local anesthetic undergarments that can be made in a variety of sizes to fit users of varying age and size.

Other features and advantages are inherent in the undergarment and method claimed and disclosed or will become apparent to those skilled in the art from the following detailed description and its accompanying drawings.

DETAILED DESCRIPTIONS OF THE DRAWINGS

In the following detailed description of the preferred embodiment, reference is made to the accompanying drawings that form a part hereof, and in which is shown by way of illustration a specific embodiment in which the invention may be practiced. It is to be understood that other embodiments may be utilized and structural changes may be made without departing from the scope of the present invention.

In the following detailed description of various embodiments of the invention, numerous specific details are set forth in order to provide a thorough understanding of various aspects of one or more embodiments of the invention. However, one or more embodiments of the invention may be practiced without these specific details. In other instances, well-known methods, procedures, and/or components have not been described in detail so as not to unnecessarily obscure aspects of embodiments of the invention.

In the following description, certain terminology is used to describe certain features of one or more embodiments of the invention. For instance "undergarment" refers to any of various coverings for the mid to lower body designed to be worn under an outer layer of clothing, such as women's panties or men's briefs. "Undergarment" can also refer to an article of clothing designed to be worn in situations where an outer layer of clothing is not necessary, such as a swimming suit. "Local anesthetic" refers to any topical anesthetic or analgesics including: amine or ester-type local anesthetics, such as benzocaine, butamben, dibucaine, lidocaine, oxybuprocaine, pramoxine, proparacaine, alcaine, procaine, proxymetacaine, and tetracaine; narcotics; nonsteroidal anti-inflammatory drugs, such as ketoprofens, Ibuprofen, and salicylates; and paracetamols, such as acetaminophen.

Figure 1:
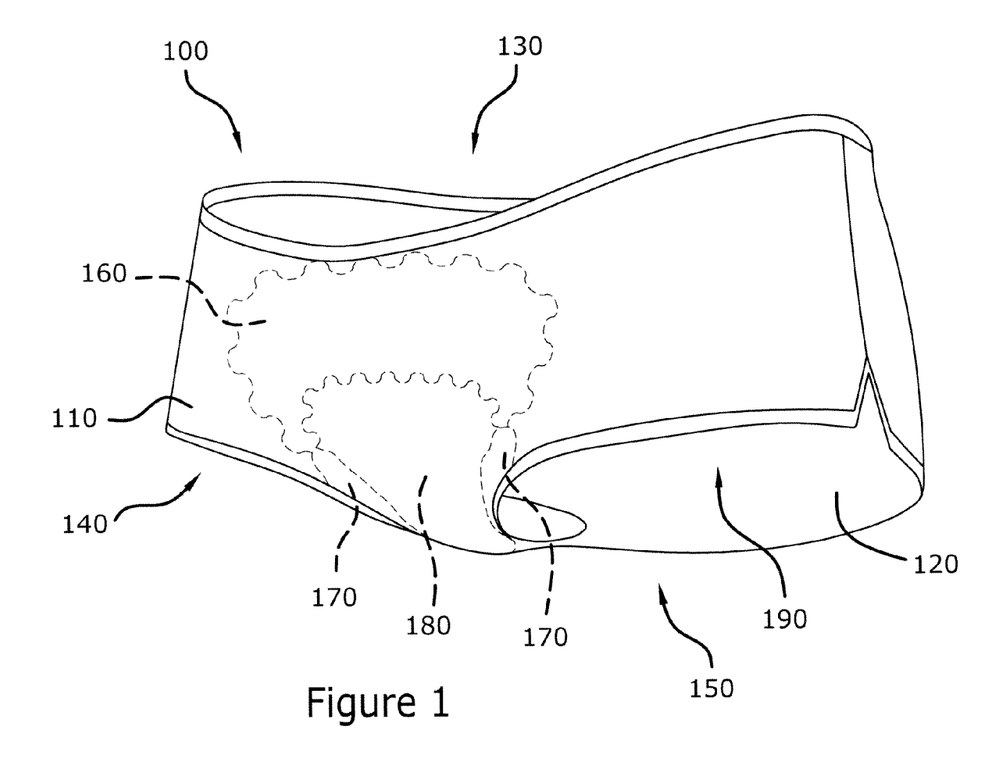
FIG. 1 is a perspective illustration of the outside of the disposable undergarments.

FIG. 1 is a perspective illustration of the outside of the disposable undergarments. A disposable undergarment 100 is shown, which features an outer portion 110 and an inner portion 120. Disposable undergarment 100 is preferably made from a natural and biodegradable material. However disposable undergarment 100 can be made from any natural or synthetic material that can accomplish the goal of serving as a temporary and disposable undergarment for the delivery of a local anesthetic, including but not limited to rubber, latex, plastic, cellophane, cotton, resin infused cotton, paper or other wood pulp based materials, wax or other resin infused paper, wool, DACRON, nylon, silk, polyester, or any combination of these materials. Disposable undergarment 100 is preferably an unobtrusive undergarment that has a torso opening 130, a right leg opening 140, and a left leg opening 150. Disposable undergarment 100 preferably covers portions of some or all of the user's legs, groin, crotch, buttocks, and torso. Disposable undergarment 100 can cover a wide range of the user's skin surface area, from a substantial portion to a minimal portion. However, disposable undergarment 100 preferably covers substantially all of the groin, crotch, and buttocks. The inner portion 120 is preferably divided into a plurality of regions including the pubis 160, the inner thighs 170, and the genital 180. This division of the inner portion 120 allows the user to apply a local anesthetic to a specific area or different anesthetics or differing concentrations of the same anesthetic to different body parts or body regions of the user. Some of the inner portion 120 regions, such as the buttocks 190, are preferably not lined with any anesthetic. Those areas that are subsequently numbed can then undergo painful procedures, such as hair removal waxing, with minimum discomfort.

Figure 2:
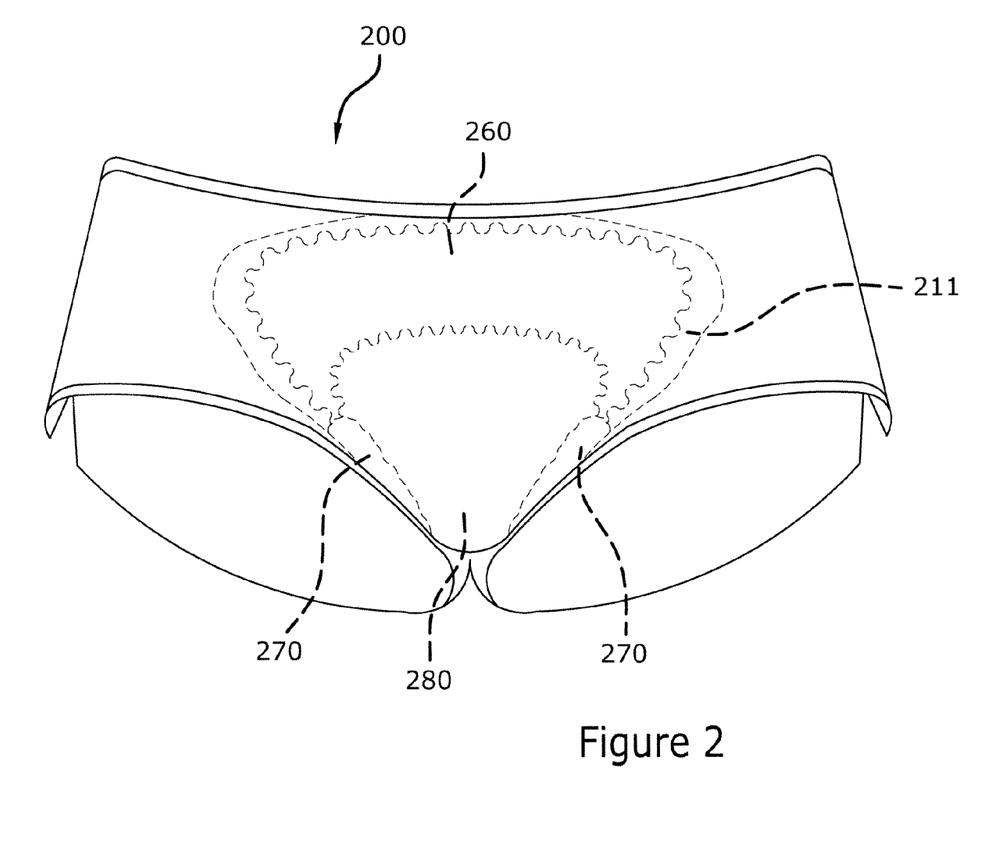
FIG. 2 is an illustration of the outside front view of the disposable undergarments.

FIG. 2 is an illustration of the outside front view of the disposable undergarments. In this view disposable undergarment 200 has an outer portion 211 that is impermeable to the local anesthetic or anesthetics that line the pubis 260, the inner thighs 270, and the genital 280 regions. Preferably disposable undergarment 200 is impermeable only in those specific areas that are lined with a local anesthetic. This impermeability prevents the local anesthetic from being absorbed by the clothing worn over disposable undergarment 200. This impermeability allows disposable undergarment 200 to act an occlusive dressing. As such, the outer clothing is not stained and the local anesthetic is not inadvertently removed.

Figure 3:
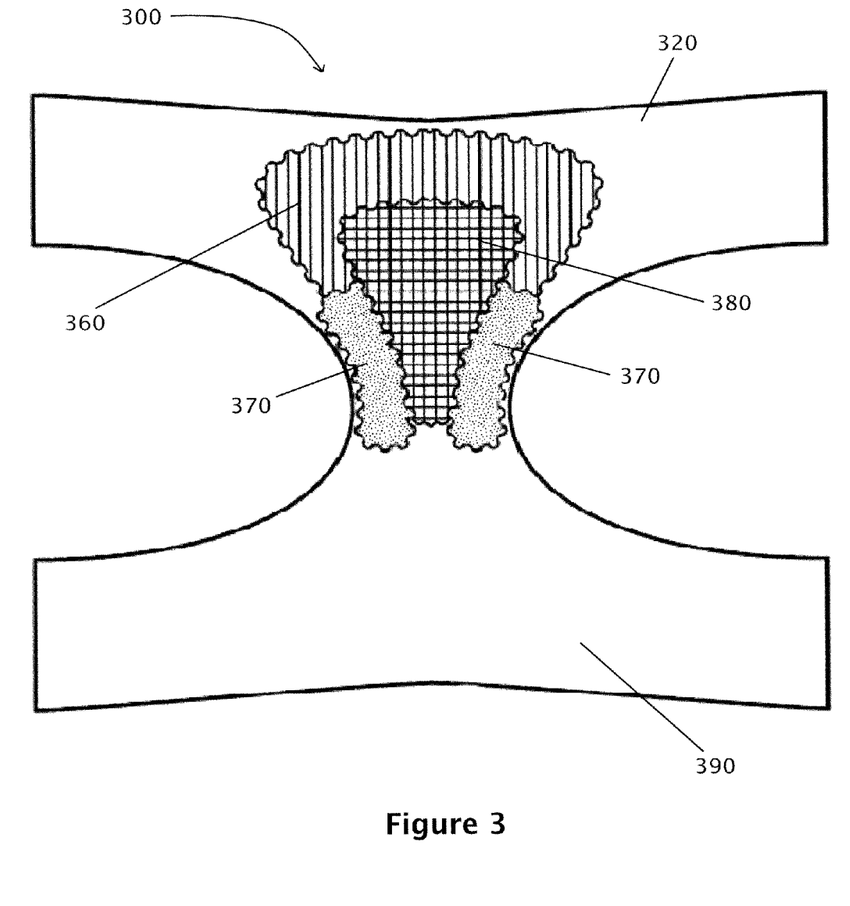
FIG. 3 is an illustration of an inside plan view of the disposable undergarments shown in a disassembled configuration.

FIG. 3 is an illustration of an inside plan view of the disposable undergarments shown in a disassembled configuration. In this view the entire surface area of the inner portion 320 of disposable undergarment 300 is visible. This detailed view shows how the inner portion 320 is preferably divided into a plurality of regions including the pubis 360, the inner thighs 370, and the genital 380. This division of the inner portion 320 allows the user to apply different anesthetics or differing concentrations of the same anesthetic to different body parts or body regions of the user. Some of the inner portion 320 regions, such as the buttocks 390, are preferably not lined with any anesthetic.

Figure 4:
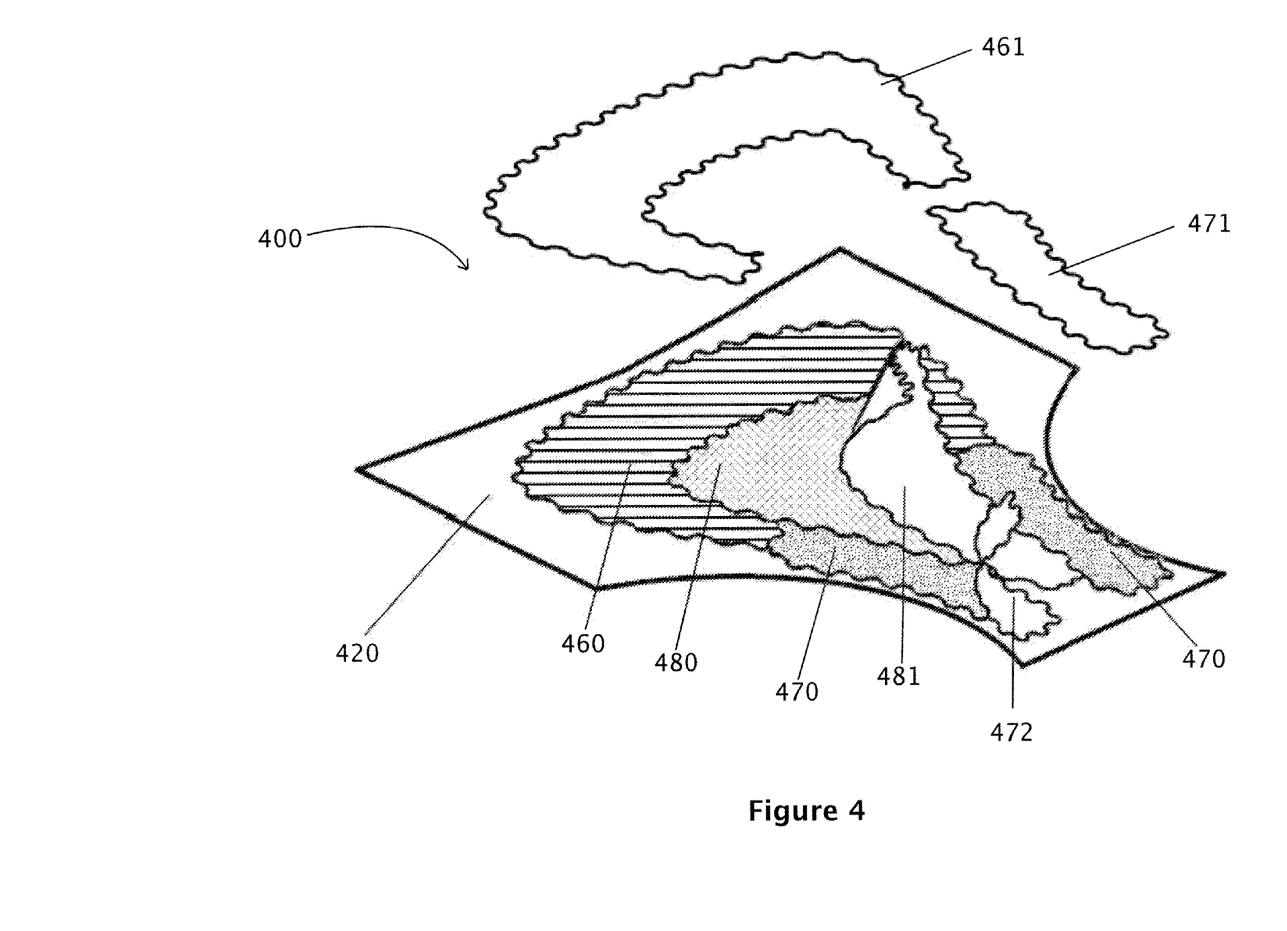
FIG. 4 is a close-up, perspective illustration of the inside front view of the disposable undergarments shown with removable covers lifted away from corresponding panel regions of the inner portion.

FIG. 4 is close-up, perspective illustration of the inside front view of the disposable undergarments shown with removable covers lifted away from corresponding panel regions of the inner portion. This detailed view shows how the inner portion 420 is preferably divided into a plurality of regions including the pubis 460, the inner thighs 470, and the genital 480. This division of the inner portion 420 allows the user to apply different anesthetics or differing concentrations of the same anesthetic to different body parts or body regions of the user. Preferably, the plurality of regions of the inner portion 420 will be pre-lined with a local anesthetic. In order to protect the local anesthetic or anesthetics that line the regions of the inner portion 420, the regions are preferably separately covered by a removable cover. In this illustration, the pubis 460, the inner thighs 470, and the genital 480 regions are lined with a local anesthetic and covered by removable covers. The pubis removable cover 461 covers the pubis 460, the inner thighs removable covers 471 and 472 cover the inner thighs 470, and the genital removable cover 481 covers the genital 480. FIG. 4 shows that the pubis removable cover 461 and one of the two inner thighs removable covers 471 have been completely removed from the pubis 460 and part of the inner thigh 470. This illustration also shows the genital removable cover 481 and one of the two inner thigh removable covers 472 in the process of being removed from the genital 480 and part of the inner thigh 470. After the removable covers are removed the user's skin will come into direct contact with the local anesthetic when the disposable undergarment 400 is donned. If the user chooses not to remove some of the removable covers, the covers will prevent the local anesthetic from numbing those areas. The removable covers are preferably made from cellophane, but they can be made from any natural or synthetic material including, but not limited to, plastic, rubber, latex, wax paper, paper, cotton, resin infused cotton, polyester, and any combination of these materials.

Figure 5:
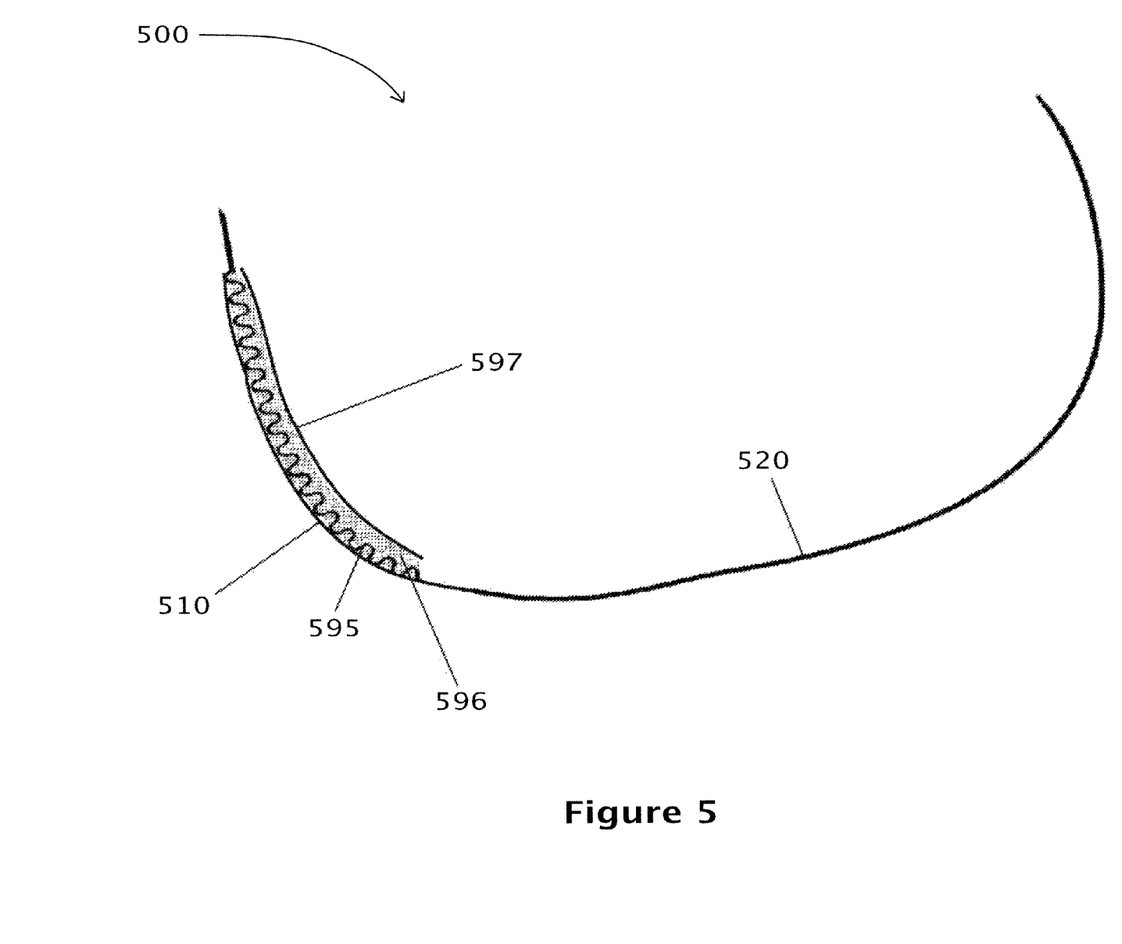
FIG. 5 is a perspective illustration of a sagittal view of the disposable undergarments, which details the corrugations of the disposable undergarments.

FIG. 5 is a perspective illustration of a sagittal view of the disposable undergarments, which details the corrugations of the disposable undergarments. In this view disposable undergarment 500 has an outer portion 510 and an inner portion 520. Inner portion 520 has a corrugated region 595 in the front of disposable undergarment 500. Preferably, corrugated region 595 is lined with a local anesthetic, such that the local anesthetic 596 fills the pockets of the corrugations. As the user wears disposable undergarment 500, the local anesthetic 596, oozes out of corrugated region 595 and is absorbed percutaneously into the wearers skin. This view also shows removable cover 597, which is peeled off of disposable undergarment 500 before donning. Removable cover 597 protects both the freshness of local anesthetic 596 and protects the user from inadvertent exposure to the local anesthetics before disposable undergarment 500 is donned.

In summary, the present invention provides a disposable local anesthetic undergarment and a method for delivering a local anesthetic to a body part. The disposable undergarments comprise an outer portion and an inner portion lined with local anesthetic, such that the inner portion has a plurality of regions that are separately covered and the outer portion is impermeable to the local anesthetic.

The foregoing description of the preferred embodiment of the invention has been presented for the purposes of illustration and description. While multiple embodiments are disclosed, still other embodiments of the present invention will become apparent to those skilled in the art from the above detailed description, which shows and describes illustrative embodiments of the invention. As will be realized, the invention is capable of modifications in various obvious aspects, all without departing from the spirit and scope of the present invention. Accordingly, the detailed description is to be regarded as illustrative in nature and not restrictive. Also, although not explicitly recited, one or more embodiments of the invention may be practiced in combination or conjunction with one another. Furthermore, the reference or non-reference to a particular embodiment of the invention shall not be interpreted to limit the scope the invention. It is intended that the scope of the invention not be limited by this detailed description, but by the claims and the equivalents to the claims that are appended hereto.

What is claimed is:

1. A method for delivering a local anesthetic to a body part comprising:

applying said local anesthetic to an inner portion of a disposable undergarment having a corrugated region in a front portion of said disposable undergarment, wherein said local anesthetic is temporarily contained within at least one pocket of said corrugated region, wherein the disposable undergarment comprises an outer portion that is impermeable to the local anesthetic at least in the areas that are lined with the local anesthetic; and covering said body part with said disposable undergarment, wherein said local anesthetic subsequently migrates from said corrugated region and is thereby absorbed percutaneously into said body part;

wherein said local anesthetic numbs said body part.

2. The method for delivering said local anesthetic to said body part according to claim 1, further comprising:

applying said local anesthetic to said inner portion in differing concentrations to a plurality of regions of said inner portion.

3. The method for delivering said local anesthetic to said body part according to claim 1, further comprising:

applying said local anesthetic to a region of the groin.

4. The method for delivering said local anesthetic to said body part according to claim 3, wherein the region of the groin includes at least one of a pubis region, an inner thigh region, and a genital region.

5. The method for delivering said local anesthetic to said body part according to claim 1, wherein said disposable undergarment functions in the same manner as an occlusive dressing.

\* \* \* \* \*